(12) United States Patent
Gottsche et al.

(10) Patent No.: US 11,484,720 B2
(45) Date of Patent: Nov. 1, 2022

(54) ELECTROMEDICAL ADAPTER, ELECTROMEDICAL ELECTRODE AND ELECTROMEDICAL PULSE GENERATOR

(71) Applicant: Osypka AG, Rheinfelden-Baden (DE)

(72) Inventors: Thorsten Gottsche, Rheinfelden (DE); Maik Grafe, Rheinfelden (DE)

(73) Assignee: Osypka AG, Rheinfelden-Baden (DE)

( * ) Notice: Subject to any disclaimer, the term of this patent is extended or adjusted under 35 U.S.C. 154(b) by 162 days.

(21) Appl. No.: 16/615,512

(22) PCT Filed: May 23, 2018

(86) PCT No.: PCT/EP2018/063564
§ 371 (c)(1),
(2) Date: Nov. 21, 2019

(87) PCT Pub. No.: WO2018/215564
PCT Pub. Date: Nov. 29, 2018

(65) Prior Publication Data
US 2020/0230424 A1    Jul. 23, 2020

(30) Foreign Application Priority Data
May 23, 2017 (DE) .......................... 102017111280.4

(51) Int. Cl.
*A61N 1/375* (2006.01)
*A61N 1/05* (2006.01)
*A61N 1/04* (2006.01)

(52) U.S. Cl.
CPC .......... *A61N 1/3752* (2013.01); *A61N 1/048* (2013.01); *A61N 1/0472* (2013.01); *A61N 1/0488* (2013.01); *A61N 1/05* (2013.01); *A61N 1/0529* (2013.01)

(58) Field of Classification Search
CPC . A61N 1/37; A61N 1/048; A61N 1/05; A61N 1/0472; A61N 1/0488; A61N 1/0529; A61N 1/056
See application file for complete search history.

(56) References Cited

U.S. PATENT DOCUMENTS

| | | |
|---|---|---|
| 4,161,952 A | 7/1979 | Kinney et al. |
| 5,222,506 A | 6/1993 | Patrick et al. |
| 7,292,894 B2 | 11/2007 | Belden |
| 2010/0057175 A1 | 3/2010 | McDonald et al. |
| 2015/0165217 A1* | 6/2015 | Hughes ................ A61N 1/0558 439/625 |

FOREIGN PATENT DOCUMENTS

| | | |
|---|---|---|
| DE | 4119222 | 12/1992 |
| GB | 2456441 | 7/2009 |
| WO | 0051489 | 9/2000 |

* cited by examiner

*Primary Examiner* — Paula J Stice
(74) *Attorney, Agent, or Firm* — Volpe Koenig

(57) ABSTRACT

An electromedical adapter, an electromedical electrode and an electromedical pulse generator are provided for the field of medical electrical stimulation. In order to connect a non-coiled electrode portion (3) to a coiled electrode portion (2), in particular the adapter (1) is provided, having at least one contact element (5) which can be contacted by a coiled electrode portion (2) of an electrode (4) in such a way that the coiled electrode portion (2) surrounds, i.e. radially surrounds, a longitudinal axis of the main body (7) of the adapter with the at least one coiled conductor (8) thereof.

20 Claims, 2 Drawing Sheets

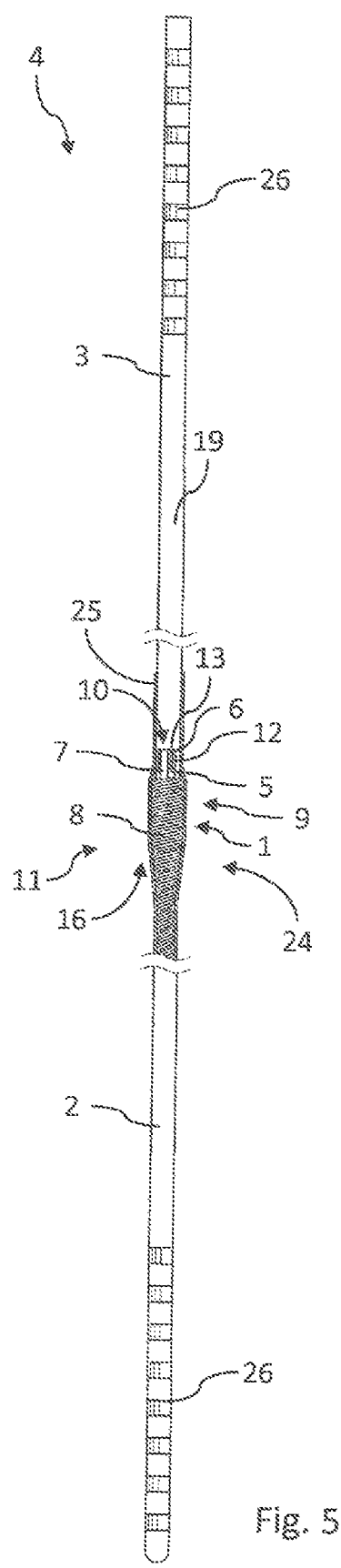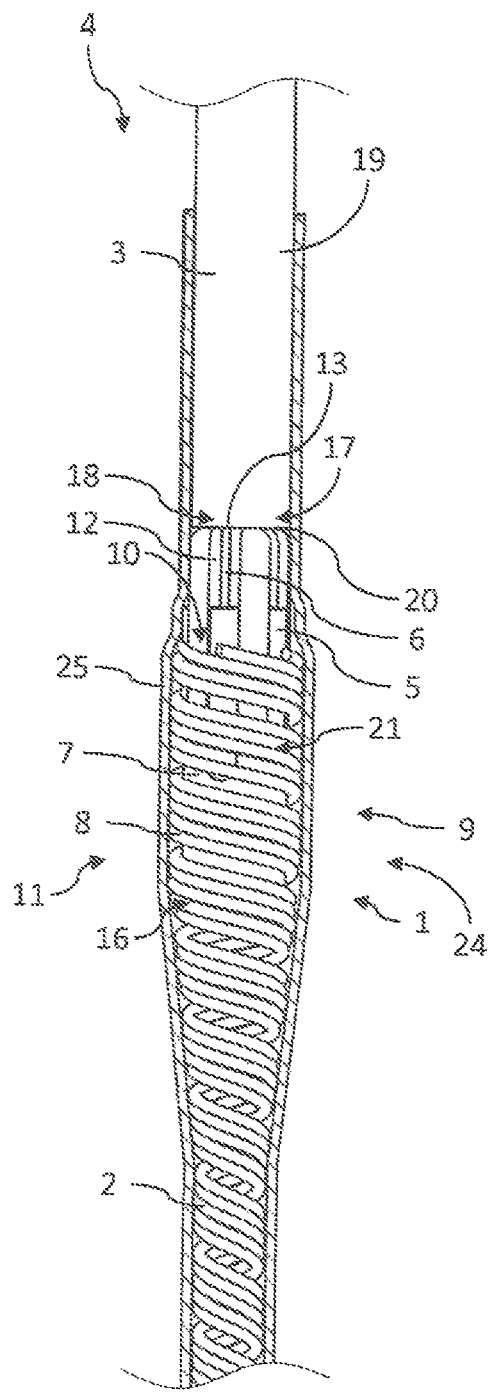
Fig. 5
Fig. 6

ELECTROMEDICAL ADAPTER, ELECTROMEDICAL ELECTRODE AND ELECTROMEDICAL PULSE GENERATOR

TECHNICAL FIELD

The invention relates to an electromedical adapter for the electrical connection of a coiled electrode portion to an uncoiled electrode portion of an electromedical electrode.

The invention further relates to an electromedical electrode, in particular an implantable electromedical electrode, and to an electromedical pulse generator which has an electromedical electrode for delivering electromedical stimulation pulses to a patient. The pulse generator can be an electromedical stimulation device, in particular an implantable electromedical stimulation device.

BACKGROUND

Such electrodes and electromedical pulse generators are known in different embodiments from the prior art.

Different electrode forms are used. Particularly where a high degree of flexibility and a high degree of resistance to fracture of the electrodes is of interest, use is made of what are called coiled electrodes, which have at least one coiled electrical conductor, that is to say an electrical conductor wound in a helical line.

Such coiled electrodes can be implanted in particular in regions of the body that are subject to strong movements, for example in the transition region between the trunk and head of a patient. They are suitable for this purpose because they tolerate movements and alternating loads comparatively well, and they do so without breaking.

However, the flexibility gained by the winding or coiling of the electrical conductors of these electrodes is associated with a greater conductor length than is necessary in the case of uncoiled electrodes with uncoiled, straight electrical conductors. Since the electrical resistance of the electrode and of its conductors increases with the length of the conductors, coiled electrodes have a higher electrical resistance compared to uncoiled electrodes with uncoiled electrical conductors. Moreover, due to their winding or coiling, they are more complicated and therefore more expensive to produce. By comparison, uncoiled electrodes have a lower electrical resistance and are easier to produce, but they are not as flexible and resistant to fracture as coiled electrodes.

SUMMARY

The object of the invention is to make available an electromedical adapter and an electromedical electrode which are of the type mentioned at the outset and which simplify the production, handling and use of such electrodes.

To achieve said object, a medical adapter is provided having one or more features of the invention directed to an electromedical adapter. In particular, in order to achieve this object, an electromedical adapter for the electrical connection of a coiled electrode portion to an uncoiled electrode portion of an electromedical electrode is provided having at least one contact element which is connectable to an uncoiled conductor of the uncoiled electrode portion and is arranged on a base body of the adapter in such a way that a coiled electrode portion contacting the at least one contact element in a position of use encloses a longitudinal axis of the base body of the adapter with its at least one coiled conductor. Preferably, the adapter has a plurality of contact elements, which can preferably be distributed uniformly on the base body, in particular uniformly distributed about the longitudinal axis of the adapter. In this way, a plurality of contact elements of the adapter are available for the coiled electrode portion. It can thus be ensured that at least one coiled conductor of the coiled electrode portion contacts one of the contact elements when the coiled electrode portion encloses the longitudinal axis in its position of use on the adapter.

The at least one coiled conductor can radially surround the longitudinal axis of the base body of the adapter and, in the position of use, can touch and thus electrically contact at least one contact element of the adapter. The aforementioned longitudinal axis of the base body of the adapter can be a longitudinal center axis of the base body of the adapter. In this way, an adapter is made available with which a sufficiently stable and above all easy to produce electrical connection between an uncoiled electrode portion and a coiled electrode portion of an electromedical electrode can be produced. The adapter makes it possible to easily produce tailor-made electrodes that combine the advantages of coiled electrodes and uncoiled electrodes.

In one embodiment of the electromedical adapter, provision can be made that the base body of the adapter has a plug-in region. At least one contact element of the adapter can be arranged on an outer side of the plug-in region, where it is easily accessible for contacting at least one coiled conductor of the coiled electrode portion. The adapter can be plugged with its plug-in region into an inner longitudinal cavity, defined by the at least one coiled conductor, in an attachment end of the coiled electrode portion for contacting the coiled electrode portion. The plugging-in can be reversibly or irreversibly detachable. In this way, reliable contact can be established between the at least one contact element of the electromedical adapter and the at least one coiled conductor of the coiled electrode portion.

It is also possible that the base body of the adapter has a socket for receiving an attachment end of the coiled electrode portion. The at least one contact element or a plurality of contact elements of the adapter for contacting the at least one coiled conductor can be arranged inside the socket. The socket can be configured in such a way that it can accommodate within it an attachment end of the coiled electrode portion. If the attachment end of the coiled electrode portion is positioned in the socket of the adapter, it comes into contact with the correspondingly arranged contact element of the electromedical adapter. This is such that an electrical connection is produced between the at least one contact element of the electromedical adapter and the at least one coiled conductor of the coiled electrode portion.

It can be advantageous if the base body of the adapter is made of an electrically insulating material. It is also possible that the adapter has on its base body, for each contact element, an in particular groove-shaped retaining seat. In this way, with the aid of the retaining seats, one or more contact elements can be secured safely and in a defined manner on the base body of the adapter. Here, one contact element can be inserted into one retaining seat. Depending on the variant of the adapter, provision can be made that at least one retaining seat is arranged on the plug-in region and/or at least one retaining seat is arranged within the socket.

Particularly simple contacting between the conductors of the two different electrode portions with the aid of the adapter is possible if the at least one contact element of the adapter is a contact sleeve. In the position of use, the latter can be inserted into a retaining seat, for example the aforementioned retaining seat, of the adapter. The retaining seat can then also be referred to as a sleeve seat. In the position of use, the at least one contact element can protrude radially outward or inward from the retaining seat for contacting the at least one coiled conductor of a coiled electrode portion. In this way, it is possible for the attachment end of the coiled electrode portion with its at least one coiled conductor to be made to touch the at least one contact element under a certain radial pressure, either radially from the inside in the case of an adapter with socket or radially from the outside in the case of an adapter with a plug-in region on whose outer side one or more contact elements are arranged. Moreover, the at least one contact element can be arranged in this way such that it is easily accessible for electrical contacting.

In an adapter which, in particular on the outer side of its plug-in region, has a retaining seat for an electrical contact element, this retaining seat can have an end-face opening through which the electrical contact element positioned in the retaining seat is accessible to an uncoiled conductor of the uncoiled electrode portion. The uncoiled conductor can be guided through this opening and connected to the contact element in the retaining seat.

Here, the end-face opening can be dimensioned such that both the contact element formed as a contact sleeve and also the uncoiled conductor can be inserted through it into the retaining seat.

Reliable contacting of one or more coiled conductors of a coiled electrode portion is possible if the adapter has a plurality of contact elements and/or retaining seats preferably distributed uniformly about a longitudinal axis of the adapter. A respective contact element can be arranged in each of the retaining seats. Particularly preferably, the adapter can have as many retaining seats as the uncoiled electrode portion to be connected to the adapter has uncoiled conductors. Thus, a respective contact element is available for each uncoiled conductor of the uncoiled electrode portion.

If the one or more contact elements are configured as contact sleeves, it is possible to electrically connect the one or more uncoiled conductors to the contact sleeve by inserting their conductor ends into the respective contact sleeve. The inserted conductor end of an uncoiled conductor can for example be welded, soldered, crimped or also glued or bonded to the contact element, in particular secured by wire bonding.

If the adapter has a plurality of retaining seats with contact elements located therein, a coiled conductor can contact a plurality of contact elements of the adapter simultaneously. In this way, the safety and reliability of the electrical connection between the adapter and the coiled electrode portion of the electromedical electrode can be further improved.

It can be advantageous if the adapter is configured for reversibly detachable connection to a coiled electrode portion. Simple replacement of the electrode portion or also of the adapter is then possible.

A good arrangement of the at least one coiled conductor on the contact element assigned to it is possible if the at least one contact element, in particular the contact sleeve, has a latching groove. At least one coiled conductor of the coiled electrode portion can latch or be latched into this latching groove when the coiled electrode portion is in the position of use on the adapter. Depending on the design of the latching groove, even haptic feedback during mounting of the adapter onto a coiled electrode portion of an electromedical electrode is possible when the coiled conductor latches into the latching groove. The latching can be effected, for example, by a radially outwardly directed movement of the coiled conductor into the latching groove, if the adapter has a socket with a contact element arranged therein.

If the adapter is one that has a plug-in region on whose outer side a contact element, in particular a contact sleeve, is provided with such a latching groove, the at least one coiled conductor of the coiled electrode portion can slide with a radially inwardly directed movement into the latching groove and latch into place there.

In a further embodiment of the electromedical adapter, the base body of the adapter can be produced from an adapter portion of a printed circuit board film that is rolled up to form a hollow body. The at least one contact element of the electromedical adapter can be an electrical contact surface formed on the adapter portion. Depending on the winding direction or rolling direction for producing the hollow body, the at least one contact element can then be arranged on an inner side of the hollow body or on an outer side of the hollow body. If the at least one contact element is arranged inside the hollow body, the hollow body, which forms the base body of the adapter, can function as a socket for receiving an attachment end of a coiled electrode portion that is to be connected to the adapter.

The hollow body can be a cylindrical hollow body having a round or circular cross section. Using a hollow body with an angular or polygonal cross section as the base body of an adapter can be favorable for an easy-to-reach arrangement of the at least one contact element. Particularly when the at least one contact element is arranged in a region of a corner or edge of the angular base body, on the outside of the hollow body forming the base body, it can protrude slightly from the base body and be reliably contacted.

If the at least one contact element is arranged on the outer side of the base body of the adapter, this region, in which the contact surface of the adapter portion acting as contact element is arranged, functions as a plug-in region. With this plug-in region, the adapter can be plugged into an inner longitudinal cavity at an attachment end of a coiled electrode portion.

In the case of a base body produced from an adapter portion of a printed circuit board film which is rolled up to form a cylindrical hollow body and which has at least one inner contact element, it can be advantageous if the adapter portion of the printed circuit board film is provided with at least one aperture. This aperture can serve as a window through which the at least one contact surface, particularly if arranged within the socket, is accessible from the outside. In this way, a coiled conductor of a coiled electrode portion can, for example by welding, soldering or gluing or also by bonding, in particular by wire bonding, be firmly connected to the contact element within the thereby defined socket of the electromedical adapter. For wire bonding, it can be advantageous if a conductor end of the at least one coiled conductor to be connected by wire bonding is flattened. The flattening of the conductor ends can be effected, for example, by rolling or hammering.

In all embodiments of the electromedical adapter, it can be advantageous if the base body of the adapter is cylindrical. In this way, the base body of the adapter can be pushed, for example with its plug-in region, optimally and with a precise fit into an inner longitudinal cavity of an attachment end of a coiled electrode portion. If the cylindrical base body of the adapter has a cylindrical socket, the attachment end of the coiled electrode portion can be brought to bear with an exact fit on the inner wall of the socket and/or contact elements arranged therein. Furthermore, an adapter with a cylindrical base body can permit a stepless transition between the two electrode portions. This is especially the case when a maximum external diameter of the adapter is adapted to the external diameters of the two electrode portions.

It can be expedient if the plug-in region of the adapter has a smaller diameter than the rest of the base body. Thus, the plug-in region of the adapter can be stepped, and the attachment end of the coiled electrode portion pushed onto the plug-in region forms a stepless outer surface together with the adapter. In this case, a stepless transition can be present between the coiled electrode portion, the adapter and the uncoiled electrode portion.

The base body of the adapter can have a round or circular cross section, particularly in its plug-in region. Moreover, the base body, at a free end of the plug-in region, can have a chamfer or a rounding for facilitated plugging or insertion of the adapter into an inner longitudinal cavity of an attachment end of a coiled electrode portion. In principle, the base body of the adapter can also have an angular or polygonal cross section. This also in its plug-in region.

To be able to secure the adapter to an uncoiled electrode portion, the adapter can have, on its base body, a plug element corresponding to a mating plug element of an uncoiled electrode portion. Thus, in the position of use, the adapter can be connected to the uncoiled electrode portion via a plug connection. In this way, a connection of the adapter to the uncoiled electrode portion is stabilized and is thus also able to withstand greater loads.

In a medical electrode of the type mentioned at the outset, the abovementioned object is achieved by the means and features of an electrode with one or more features of the invention. In particular, in order to achieve this object, an electromedical electrode is provided having at least one coiled electrode portion and at least one uncoiled electrode portion, wherein the coiled electrode portion comprises at least one coiled electrical conductor and the uncoiled electrode portion comprises at least one uncoiled electrical conductor, and wherein the two electrode portions are electrically connected to each other via an adapter.

In this way, an electromedical electrode is created which combines the advantages of the two different types of electrode. Thus, it is possible to route the uncoiled electrode portion of the electromedical electrode for example in a body part which is not greatly moved, such that here the uncoiled electrode portion is subjected to comparatively low loads, which it is able to tolerate. The coiled and therefore more flexible electrode portion can be routed particularly in body regions that are subject to relatively strong movements. The electromedical electrode thus created is sufficiently flexible and resistant to breakage caused by alternating loads, and yet it has a lower electrical resistance than those electrodes that are produced exclusively from coiled conductors. The connection between the two electrode portions can be made particularly reliable and stable if the adapter used is an adapter having one or more of the above-noted features.

If the coiled electrode portion is connectable, and in the position of use connected, to the adapter in a reversibly detachable manner, the coiled electrode portion can be exchanged, if necessary, and replaced by another one. Exchange of the adapter can thus also be permitted.

In one embodiment of the electrode according to the invention, the at least one coiled conductor of the coiled electrode portion can engage externally over the adapter in order to contact the uncoiled electrode portion. In this case, the at least one coiled conductor of the coiled electrode portion can engage externally over a or the plug-in region of the adapter for contacting the uncoiled electrode portion. Here, the adapter thus functions as a plug-in part which can be plugged into an inner longitudinal cavity defined by the coiled conductor of the coiled electrode portion, in order to establish an electrical contact between the coiled conductor and the uncoiled conductor of the uncoiled electrode portion. Mounting of the electrode is thus simplified.

However, it is also possible that the coiled electrode portion for contacting the uncoiled electrode portion is plugged with its attachment end into a or the socket of the adapter. This exploits the fact that the adapter has a socket for the at least one coiled conductor, into which socket the coiled electrode portion can be plugged, and in the position of use is plugged, with an end for contacting the coiled electrode portion.

As has already been mentioned above, the adapter can have at least one contact element via which the at least one coiled conductor of the coiled electrode portion is electrically connectable, and in the position of use connected, to the at least one uncoiled conductor of the uncoiled electrode portion. In this case, the at least one contact element can be arranged on an outer side of a plug-in region of the adapter and thus be accessible from outside for the coiled electrode portion. It is also possible that the aforementioned contact element or a further contact element is arranged within the socket of the adapter. Thus, the contact element is also accessible to a coiled electrode portion for contacting, which is plugged into the socket of the adapter.

In a variant of the electromedical electrode, provision is made that the uncoiled electrode portion is formed from a lumen tube with at least one inner lumen and at least one uncoiled conductor arranged in the latter. Preferably, a multi-lumen tube can also be used as an uncoiled electrode portion, which multi-lumen tube has a plurality of inner lumens, in each of which an uncoiled conductor is arranged.

The adapter can be made of an electrically insulating material and, on the outer side of its plug-in region, can have at least one retaining seat for the at least one contact element, into which retaining seat the contact element is inserted. In this way, it is possible to secure the at least one contact element on the outside of the plug-in region of the adapter and thus to permit reliable attachment of the adapter to the coiled electrode portion.

When using an uncoiled electrode portion that comprises a lumen tube, it is possible that each uncoiled conductor of the uncoiled electrode portion is connected, with a conductor end protruding from the lumen tube, to a contact element, preferably a respective contact element, of the adapter. The connection of the respective conductor end to the contact element can in this case be done, for example, by crimping, by soldering, by welding, by bonding, by wire bonding, by spring force and/or by gluing. A connection of the respective conductor end to the contact element by crimping is possible particularly when the contact element is designed as a contact sleeve. In this way, the respective conductor end of the uncoiled conductor can first be pushed into the interior of the contact sleeve and then connected to the contact sleeve by crimping of the latter.

The at least one coiled conductor of the coiled electrode portion can be connected to the at least one contact element by welding, gluing, soldering and/or bonding or wire bonding. If the at least one coiled conductor of the coiled electrode portion is connected to the at least one contact element by spring force, the coiled electrode portion can be particularly easily connected to the adapter in a reversibly detachable manner.

As has already been mentioned above, the adapter can have a plurality of contact elements and/or retaining seats preferably distributed uniformly about a longitudinal axis of the adapter. In this case, a respective contact element connected to an uncoiled conductor can be arranged in each of the retaining seats. Preferably, the adapter has as many retaining seats as the uncoiled electrode portion has uncoiled conductors. In this way, exactly one retaining seat is available for each uncoiled conductor of the uncoiled electrode portion, into which retaining seat a contact element, preferably a contact sleeve, is insertable.

A reliable electrical connection of the two electrode portions can be achieved if the at least one coiled conductor of the coiled electrode portion contacts at least two contact elements of the adapter in the position of use. A particularly reliable electrical connection of the two electrode portions can be achieved if, in the position of use on the adapter, the at least one or each coiled conductor of the coiled electrode portion contacts each contact element of the adapter at least once. For this purpose, it can be advantageous if the one or more coiled conductors radially surround the adapter and its at least one contact element in the position of use over an angular range of more than 180 degrees, particularly preferably of more than 360 degrees. Thus, in the position of use, each coiled conductor can be wound at least once around the adapter. Thus, in the position of use, each coiled conductor is guided at least once past each contact element of the adapter and can contact same.

An external diameter of the coiled electrode portion, in particular of the attachment end thereof, can be greater than a diameter of an imaginary enveloping circle which, in the position of use on the adapter, envelops contact elements, in particular contact sleeves, located inside its socket. Thus, the coiled electrode portion can be arranged under radial pressure between the contact elements in the socket of the adapter. This promotes a reliable electrical connection of the electrode portions.

Furthermore, a clear internal diameter, in particular of an inner longitudinal cavity in the region of an attachment end, of the coiled electrode portion can be smaller than a diameter of an imaginary enveloping circle which, in the position of use, envelops contact elements, in particular contact sleeves, located on an outer side of the base body of the adapter, in particular in the plug-in region thereof. Thus, the coiled electrode portion can engage over the adapter and its contact elements under radial pressure. This variant is used in particular where one or more contact elements are formed on an outer side of a plug-in region of the adapter.

In both variants described above, the pressure can be chosen such that the pressure alone is able to produce a reversibly detachable or permanent plug connection between the coiled electrode portion and the adapter. It is conceivable in this context to dispense with further fastening measures such as bonding, wire bonding, gluing, soldering or welding. In both variants, the coiled electrode portion can act as a spring and apply a radially outwardly or inwardly acting spring force to generate the aforementioned pressure on the adapter. The coiled electrode portion can then be connected to the adapter with force-fit engagement.

In one embodiment of the invention, the adapter can be connected to the uncoiled electrode portion. This connection can be made particularly simply if the adapter and the uncoiled electrode portion can be plugged together and, in the position of use, are plugged together. It is conceivable here that the adapter is plugged together, for example, with the lumen tube of the electrode portion and is optionally also glued to same.

For this purpose, a plug connection can be formed between the uncoiled electrode portion and the adapter. In this plug connection, provision can be made that the adapter has a plug element which is preferably arranged at the end face and with which it can be plugged, and in the position of use is plugged, together with a correspondingly configured mating plug element on the uncoiled electrode portion, in particular on the lumen tube of the uncoiled electrode portion. After the plug connection has been produced, it can additionally be secured and strengthened by gluing or welding.

In a further embodiment of the electrode according to the invention, provision can be made that the uncoiled electrode portion is produced from a flexible printed circuit board film which, in the position of use, is rolled up to form a pipe. This printed circuit board film can have, as uncoiled conductor, at least one conductor track extending along the longitudinal extent thereof, preferably parallel to a longitudinal axis of the printed circuit board film. The use of printed circuit board films that have correspondingly applied conductor tracks can simplify the production of the uncoiled electrode portion. The pipe can have a round, circular, angular or polygonal cross section. Using a pipe with an angular or polygonal cross section can be advantageous for reliable contacting of the at least one contact element. This is especially so when the at least one contact element is arranged in the region of an outer corner or an outer edge of the pipe with angular cross section. Here, the at least one contact element then protrudes slightly and can be reliably contacted with the coiled conductor of the coiled electrode portion.

The uncoiled electrode portion, particularly if formed from a printed circuit board film rolled up to form a pipe, can have a stabilizing support element in its interior. A support tube for example can be used as the support element. Alternatively or additionally, the uncoiled electrode portion can have a stabilizing filler in its interior. This filler can consist of epoxy resin, for example.

Particularly when the uncoiled electrode portion is formed from a printed circuit board film rolled up to form a pipe, an adapter portion of the printed circuit board film can serve as the adapter.

In this case, the adapter portion for each conductor track can in each case have a contact element in the form of a contact surface electrically connected to a conductor track. Depending on the winding direction of the printed circuit board film for producing the pipe, the at least one contact surface can be arranged on an outer side of the pipe, which then functions as a plug-in region of the adapter, or on an inner side of the pipe, which then functions as a socket of the adapter. It is also possible that the contact surface is arranged on an inner wall of the pipe, which inner wall forms a socket of the adapter for the coiled electrode portion and circumferentially delimits this socket.

To make it easier for a coiled electrode portion inserted into the socket of the adapter to be secured to the at least one contact surface of the adapter portion serving as contact element, the adapter portion of the printed circuit board film can have at least one aperture. Through this aperture, the at least one contact surface of the adapter portion can be accessible from the outside.

A further special feature of the electrode is that it can be extended to almost any desired degree and permits a modular configuration. Thus, the electrode can comprise a plurality of coiled electrode portions and/or a plurality of uncoiled electrode portions, wherein two successive electrode portions are connected to each other by in each case one adapter. Thus, for example, the electrode can have a first uncoiled electrode portion and a first coiled electrode portion, which are connected to each other by an above-described adapter. The first coiled electrode portion can then in turn be connected via a further adapter to a further uncoiled electrode portion. It is thus possible to assemble electromedical electrodes of almost any desired length with successive coiled and uncoiled electrode portions.

The electrode can moreover have a protective sheath, with which the adapter and a connection site between two electrode portions are surrounded. With the aid of this protective sheath, the connection produced with the aid of the adapter between the two electrode portions can be stabilized and protected from external influences.

To achieve the object mentioned at the outset, an electromedical pulse generator, in particular an implantable electromedical stimulation device, is provided which has, as its electromedical electrode, an electromedical electrode having one or more feature of the invention.

The electromedical pulse generator can be configured as a neurostimulator, for example of the kind used and implanted as a brain pacemaker.

BRIEF DESCRIPTION OF THE DRAWINGS

The invention is now described in more detail on the basis of illustrative embodiments but is not restricted to these illustrative embodiments. Further illustrative embodiments arise through combination of the features of single or multiple protective claims with one another and/or single or multiple features of the illustrative embodiment. In the drawing, parts of which are highly schematic:

FIG. 5 shows a side view of a electrode which is comparable to the electrode shown in FIGS. 1 and 2 and which has a protective sheath that surrounds the adapter and the connection site between the two electrode portions, and FIG. 6 shows an enlarged view of the connection site between the two electrode portions from FIG. 5.

DETAILED DESCRIPTION

Figure 1:
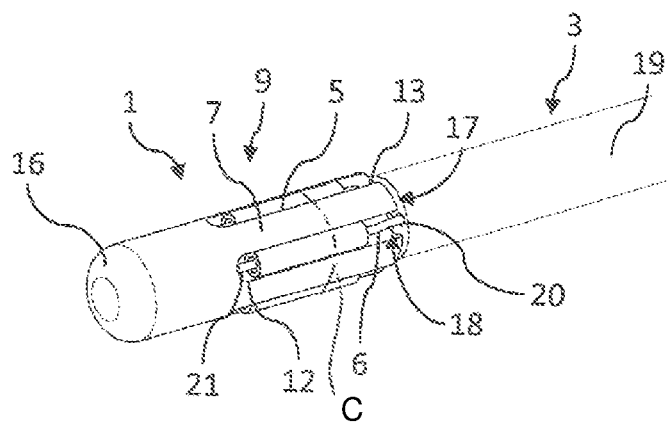
FIG. 1 shows a perspective view of an uncoiled electrode portion formed from a multi-lumen tube, with an adapter according to the invention at one end of the uncoiled electrode portion.

FIGS. 1 to 6 show different embodiments of an electromedical adapter. The adapter 1 is designated generally by 1.

In the following description, elements that correspond in terms of their function retain corresponding reference numbers even when their configuration or shape differs.

The electromedical adapters 1 shown in the figures are designed for the electrical connection of a coiled electrode portion 2 to an uncoiled electrode portion 3 of an electrode designated generally by 4. For this purpose, the adapter 1 has at least one contact element 5 which is connectable to an uncoiled conductor 6 of the uncoiled electrode portion 3 and is arranged on a base body 7 of the adapter 1 in such a way that a coiled electrode portion 2 contacting the at least one contact element 5 in the position of use radially surrounds a longitudinal axis of the base body 7 of the adapter 1 with its at least one coiled conductor 8.

The coiled electrode portion 2 shown in FIGS. 2, 4, 5 and 6 has a total of four coiled conductors 8.

Figure 2:
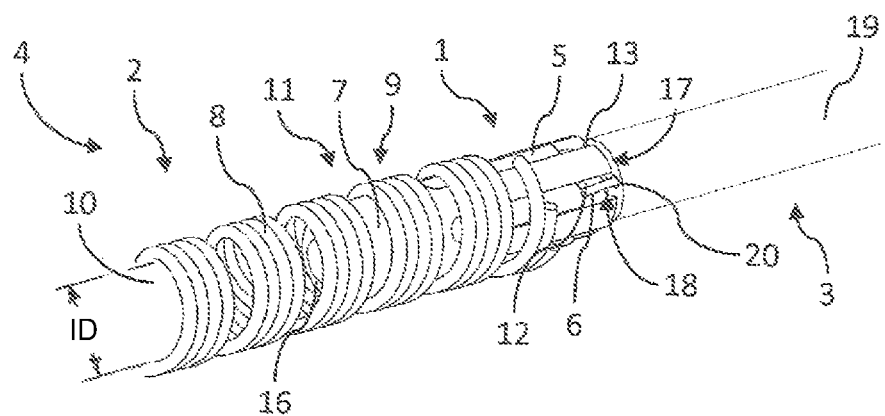
FIG. 2 shows a perspective view of an electrode according to the invention, wherein a coiled electrode portion with a total of four coiled electrical conductors is pushed over a plug-in region of the adapter shown in FIG. 1 in order to connect the coiled electrode portion to the uncoiled electrode portion likewise shown in FIG. 1, and it will be seen here that each of the coiled conductors contacts each contact element of the adapter at least once.
Figure 3:
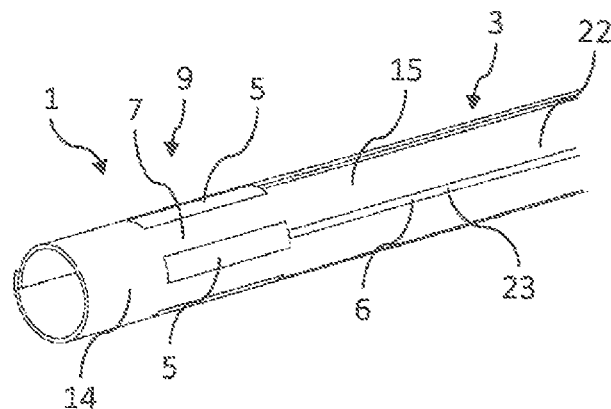
FIG. 3 shows a perspective view of an uncoiled electrode portion with an adapter region formed thereon, wherein the electrode portion and the adapter are formed by rolling up a flexible printed circuit board film into a cylindrical hollow body, here a pipe.
Figure 4:
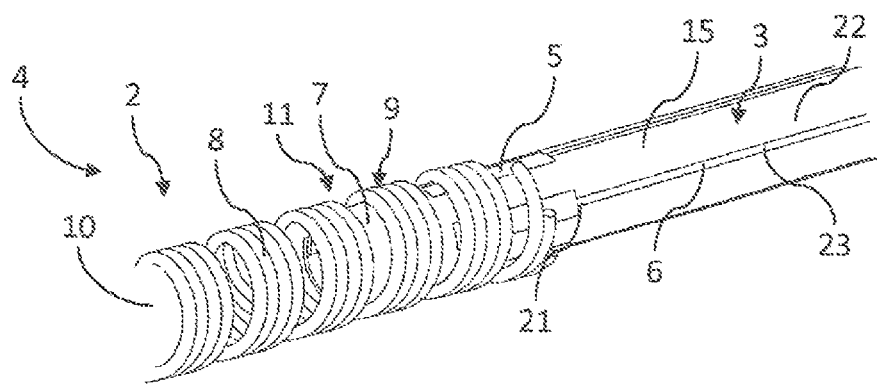
FIG. 4 shows a perspective view of an electrode according to the invention whose coiled electrode portion with its four coiled electrical conductors is pushed over the adapter region, forming an adapter of the electrode, of the printed circuit board film of the uncoiled electrode portion rolled up to form the pipe, such that the coiled conductors encircle the adapter and the plug-in region of the adapter several times and touch each contact element of the adapter at least once.

All the embodiments of the adapter 1 shown in FIGS. 1 to 6 each have a plug-in portion 9 on their base bodies 7. The total of five contact elements 5 of the respective adapter 1 are arranged on an outer side of the plug-in portion 9. As is shown in FIGS. 2 and 4, the respective adapter 1 can be inserted with its plug-in portion 9 into an inner longitudinal cavity 10, defined by the at least one coiled conductor 8 of the coiled electrode portion 2, in an attachment end 11 of the coiled electrode portion 2 in order to contact the coiled electrode portion 2 and its coiled conductor 8.

In another embodiment (not shown in the figures) of the adapter 1, provision is made that the base body 7 of this adapter 1 has a socket for receiving an attachment end 11 of the coiled electrode portion 2. In this socket, at least one contact element 5 is then arranged for contacting the at least one coiled conductor. If a plurality of contact elements 5 are present, they are preferably distributed uniformly about a longitudinal axis of the adapter 1, its base body 7 or also its socket.

The base bodies 7 of the adapters 1 shown are made of an electrically insulating material. The adapter 1 shown in FIGS. 1 and 2 has on its base body 7, for each of the contact elements 5, a respective groove-shaped retaining seat 12. In each of the five retaining seats 12 in total, a respective contact element 5 is inserted. Each of the retaining seats 12 is arranged on the plug-in portion 9 of the adapter 1.

In an adapter 1 having a socket for receiving the coiled electrode portion 2, the retaining seats 12 are arranged correspondingly within the socket. The retaining seats 12 and the contact elements 5 are uniformly distributed about a longitudinal axis of the base body 7 of the adapter 1 and thus arranged on the adapter 1 in such a way that they can be easily contacted by the coiled conductors 8 of the coiled electrode portion 2. It is noted here that the coiled conductors 8 surround the plug-in region 9 of the adapter 1, and the contact elements 5 arranged thereon, several times, that is to say in an angular range of more than 360 degrees. As a result, each of the four coiled conductors 8 contacts each of the five contact elements 5 at least once. This promotes a reliable electrical connection of the electrode portions 2 and 3.

The retaining seats 12 of the adapter 1 from FIGS. 1 and 2 have end-face openings 13. Through these end-face openings 13, the contact elements 5 can first be inserted into the retaining seats 12. Subsequently, the uncoiled conductors 6 of the uncoiled electrode portion 3 can be connected to the contact elements 5 through these end-face openings 13.

In the illustrative embodiment of the adapter 1 shown in FIGS. 1 and 2 and FIGS. 5 and 6, the contact elements 5 are contact sleeves which, in the position of use, are inserted into the retaining seats 12 of the adapter 1. In their position of use, the contact elements 5 in the form of contact sleeves protrude radially outward from the retaining seats 12 and, for contacting the total of four coiled conductors 8 of the coiled electrode portion 2, protrude outward beyond an outer circumference of the base body 7 of the adapter 1.

The adapter 1 has a plurality of contact elements 5 and retaining seats 12 uniformly distributed about a longitudinal axis of the adapter 1 and its base body 7. According to FIGS. 3 and 4, provision is also made, in the adapter 1 shown there, that a plurality of contact elements 5 are uniformly distributed about the longitudinal axis of this adapter 1.

A common feature of both adapters 1 is that they have as many retaining seats 12 or contact elements 5 as the uncoiled electrode portion 3 to be connected to the adapter 1 has uncoiled conductors 6. Thus, a contact element 5 is available for each uncoiled conductor 6 of the uncoiled electrode portion 3 and, in the adapter 1 according to FIGS. 1 and 2 and also FIGS. 5 and 6, a retaining seat 12 is also available in each case.

In particular, the contact elements 5 formed as contact sleeves can each have a latching groove on the outside. When the coiled electrode portion 2 is located in the position of use on the adapter 1, at least one of the four coiled conductors 8 of the coiled electrode portion 2 can engage in this latching groove 2 and be latched therein in the position of use.

In the illustrative embodiment of the electromedical adapter 1 shown in FIGS. 3 and 4, the base body 7 of the adapter 1 is produced from an adapter portion 14 of a flexible printed circuit board film 15. This is done by the adapter portion 14 of the flexible printed circuit board film 15 being rolled up to form a cylindrical hollow body, here a pipe.

The five contact elements 5 of this adapter 1 are contact surfaces formed on the adapter portion 14. Each of the contact elements 5 formed as contact surfaces is electrically connected to a conductor track that forms an uncoiled conductor 6 of the uncoiled electrode portion 3.

The base bodies 7 of both adapters 1 are cylindrical and have a round or circular cross section. The base body 7 of the adapter shown in FIGS. 1 and 2 is provided with a chamfer or rounding 16 in its plug-in region 9 at a free end, which functions as a plug-in end. With the aid of this rounding 16, the adapter 1 can be more easily introduced into the aforementioned inner longitudinal cavity 10 of the coiled electrode portion 2.

At an end the base body 7 of the adapter 1 opposite the rounding 16, the base body 7 has a plug element 17. A mating plug element 18 corresponding to the latter is arranged on the front end face of the uncoiled electrode portion 3. Thus, between the adapter 1 and the uncoiled electrode portion 3, a plug connection is provided via which the adapter 1 or its base body 7 can be connected to the uncoiled electrode portion 3.

The electromedical electrode 4 is configured as a stimulation electrode and, for example, can be used to deliver stimulation pulses, for example to the brain or another organ of a patient. The electromedical electrodes 4 shown in FIGS. 1 and 2 and also FIGS. 3 and 4 each comprise a coiled electrode portion 2 and an uncoiled electrode portion 3. The coiled electrode portion 2 comprises a total of four coiled electrical conductors 8, which together define the aforementioned inner longitudinal cavity 10 and enclose or encircle the latter several times. The uncoiled electrode portion 3 comprises at least one electrical conductor 6, in the present illustrative embodiment five uncoiled electrical conductors 6. The conductors 6 and 8 of the two electrode portions 2 are electrically connected to each other via one of the two adapters 1 already described above.

FIGS. 2 and 4 and also FIGS. 5 and 6 illustrate that the coiled conductors 8 of the coiled electrode portion 2 engage externally over the respective plug-in region 9 of the adapter 1 for contacting the uncoiled electrode portion 3 with an attachment end 11. In an embodiment of the electromedical electrode 4 not shown in the figures, provision is made that the coiled portion 2 is plugged with an attachment end 11 into a socket of an electromedical adapter 1 and is thereby electrically connected to the uncoiled electrode portion 3.

In the illustrative embodiments of the electromedical electrode 4 shown in FIGS. 1, 2, 5 and 6, the uncoiled electrode portion 3 is formed by a so-called multi-lumen tube 19. The latter comprises, for each of the five uncoiled conductors 6, an inner lumen 20, in each of which an uncoiled conductor 6 extends.

Each uncoiled conductor 6 of the uncoiled electrode portion 3 has a conductor end 21 protruding from the lumen tube 19. Each conductor end 21 is connected to a respective contact element 5 of the adapter 1. Since the contact elements 5 of the adapter 1 shown in FIGS. 1 and 2 are formed from contact sleeves, the conductor ends 21 can be pushed into the contact sleeves 5 and can be connected to the contact sleeves 5 by crimping the contact sleeves 5. The coiled conductors 8 of the coiled electrode portion 2 can be connected to the sleeve-shaped contact elements 5, for example by welding, gluing, soldering, bonding or wire bonding.

Each coiled conductor 8 of the coiled electrode portion 2 contacts all of the total of five contact elements 5 of the adapter 1. This applies to both of the illustrative embodiments of the adapters 1 and electrodes 4 shown in FIGS. 1 to 4.

A clear internal diameter ID of the coiled electrode portion 2, more precisely its inner longitudinal cavity 10 in the region of its attachment end 11, is smaller than a diameter of an imaginary enveloping circle (dot-dash line indicated at C in FIG. 1) which envelops the contact elements 5 located in the position of use on the outside of the plug-in region 9 of the respective adapter 1. This has the consequence that the coiled electrode portion 2 engages over the adapter 1 and its contact elements 5, in particular with its attachment end 11, under radial pressure. This permits a force-fit connection between the coiled electrode portion 2 and the adapter 1 and also a reliable fit of the coiled electrode portion 2 on the adapter 1 and a stable connection of the two electrode portions 2 and 3. The spreading that the coiled electrode portion 2 experiences in the region of its attachment end 11 can be clearly seen in the illustrative embodiment or electrode 4 shown in FIGS. 5 and 6.

In the illustrative embodiment of the electrode 4 according to FIGS. 3 and 4, the uncoiled electrode portion 3 is produced from a flexible printed circuit board film 15 which is rolled up to form a pipe 22 in the position of use. The printed circuit board film 15 has a total of five conductor tracks 23 which extend along the longitudinal extent of the printed circuit board film 15 and are oriented parallel to one another and to a longitudinal axis of the printed circuit board film 15. These conductor tracks 23 function as uncoiled conductors 6 of this form of uncoiled electrode portion 3.

The uncoiled electrode portion 3 can contain in its interior a stabilizing support element and/or a stabilizing filler, for example of epoxy resin, particularly when the uncoiled electrode portion 3 is formed from a printed circuit board film 15 rolled up to form a pipe 22.

As has already been mentioned above, the adapter 1 in the electromedical electrode 4 shown in FIGS. 3 and 4 is formed from an adapter portion 14 of the printed circuit board film 15 of the uncoiled electrode portion 3. Thus, the adapter 1 is automatically produced when the flexible printed circuit board film 15 is rolled up to produce the uncoiled electrode portion 3. The adapter portion 14 is thus part of the printed circuit board film 15 and has, for each conductor track 23, a respective contact surface electrically connected as contact element 5 to a conductor track 23. This can be seen clearly in FIGS. 3 and 4.

Depending on the direction of winding of the flexible printed circuit board film 15 for producing the uncoiled electrode portion 3, this contact surface serving as contact element 5 can then be arranged on an outer side or also on an inner side of the pipe 22 thus produced. If the at least one contact surface 5 is arranged on an inner side of the printed circuit board film 15 rolled up to form a pipe 22, this results in an adapter 1 with a socket which is suitable for receiving an attachment end 11 of a coiled electrode portion 2 to be connected to the adapter 1.

Here, the at least one contact surface 5 is then arranged on a inner wall of the pipe 22 delimiting a socket of the adapter 1 for receiving the coiled electrode portion 2.

The electrode 4 can comprise more than the two electrode portions 2 and 3 shown in the figures. Particularly where a coiled electrode portion 2 meets an uncoiled electrode portion 3 or vice versa, an adapter 1 for connecting the two electrode portions 2 and 3 is then provided in each case.

In the illustrative embodiment of the electrode 4 shown in FIGS. 5 and 6, a connection site 24 between the two electrode portions 2 and 3 is surrounded by a protective sheath 25 and is additionally stabilized by the latter. The protective sheath 25 moreover protects the electrical connection, produced with the aid of the adapter 1, between the electrode portions 2 and 3. At their ends facing away from the connection site 25, both electrode portions 2 and 3 have a plurality of electrode contacts 26. With the electrode contacts 26, one of the electrode portions 2 and 3 can be placed, for example, in a correspondingly configured connection socket of an electromedical pulse generator and attached thereto. The electrode contacts 26 of the corresponding electrode portion 2 or 3, arranged at the distal end of the electrode 4, are then implanted, for example in a target site to which electrical impulses are intended to be delivered via the electrode contacts 26.

The embodiments of the electromedical electrode 4 shown in the figures can be used on an electromedical pulse generator. The electromedical electrodes 4 can be used particularly advantageously in an implantable electromedical stimulation device, for example an electromedical neurostimulator. Such a neurostimulator is used, for example, for the stimulation of specific regions of the brain. The neurostimulator is placed in the trunk of a patient, especially in the region of the clavicle or the chest. The target site to which the stimulation pulses are to be delivered by the electrode 4 then lies in the head of the patient. In order to bridge the distance between the target site and the implantation site at which the electromedical pulse generator is implanted, the electrode 4 according to the invention is used. Here, an uncoiled electrode portion 3 can be routed in a section that is still located in the trunk of the patient. In the trunk, the electrode portion 3 is exposed to comparatively slight movements, such that an uncoiled electrode portion can be used here. In the neck region, which is by nature exposed to greater movements than the trunk, the electrode portion used can be a coiled electrode portion 2, which is more flexible and more resistant to fracture than an uncoiled electrode portion 3.

In this way, an electrode 4 is used that is tailored to the particular application. This has the advantage that, with sufficient flexibility afforded by the coiled electrode portion 2, a comparatively low total electrical resistance of the electrode 4 can be achieved through the uncoiled electrode portion 3.

The invention is concerned with improvements in the technical field of electromedical stimulation. For this purpose, an electromedical adapter 1, an electromedical electrode 4 and an electromedical pulse generator are provided. In order to connect an uncoiled electrode portion 3 to a coiled electrode portion 2, the adapter 1 in particular is provided which has at least one contact element 5, the latter being contacted by a coiled electrode portion 2 of an electrode 4 in such a way that the coiled electrode portion 2 encloses, i.e. radially surrounds, a longitudinal axis of the base body 7 of the adapter 1 with its at least one coiled conductor 8.

LIST OF REFERENCE SIGNS 1 adapter
2 coiled electrode portion
3 uncoiled electrode portion
4 electrode
5 contact element/contact sleeve/contact surface
6 uncoiled conductor
7 base body
8 coiled conductor
9 plug-in region of 1
10 inner longitudinal cavity of 2
11 attachment end of 2
12 retaining seat
13 end-face opening of 12
14 adapter portion
15 printed circuit board film
16 rounding
17 plug element on 1
18 mating plug element on 19
19 lumen tube/multi-lumen tube
20 lumen
21 conductor end
22 pipe
23 conductor track
24 connection site
25 protective sheath
26 electrode contacts

The invention claimed is:

1. An electromedical adapter (1) for an electrical connection of a coiled electrode portion (2) to an uncoiled electrode portion (3) of an electromedical electrode (4), the adapter (1) comprising:
   a base body (7),
   at least one contact element (5) which is connectable to an uncoiled conductor (6) of the uncoiled electrode portion (3) and is arranged on the base body (7) such that the coiled electrode portion (2) directly contacts the at least one contact element (5) in a position of use and encloses a longitudinal axis of the base body (7) of the adapter (1) with at least one coiled conductor (8) thereof.

2. The electromedical adapter (1) as claimed in claim 1, wherein the base body (7) has a plug-in region (9), and the at least one contact element (5) is arranged on an outer side of the plug-in region (9), and the adapter (1) is configured to be plugged with said plug-in region (9) into an inner longitudinal cavity (10), defined by the at least one coiled conductor (8), in an attachment end (11) of the coiled electrode portion (2) for contacting the coiled electrode portion (2).

3. The electromedical adapter (1) as claimed in claim 2, wherein at least one of (a) the base body (7) is made of an electrically insulating material, or (b) at least one respective retaining seat (12) into which a contact element (5) is insertable or inserted, is arranged on the base body (7).

4. The electromedical adapter (1) as claimed in claim 1, wherein the at least one contact element (5) is a contact sleeve which, in the position of use, is inserted into a retaining seat (12) of the base body (7), and the at least one contact element (5) in the position of use protrudes radially outward or inward from the retaining seat (12) for contacting the at least one coiled conductor (8) of the coiled electrode portion (2).

5. The electromedical adapter (1) as claimed in claim 4, wherein there are a plurality of at least one of the contact elements (5) or the retaining seats (12) distributed about a longitudinal axis of the adapter (1), and one of the contact elements (5) is arranged in each of the retaining seats (12), and the adapter (1) is adapted to have as many of at least one of the contact elements (5) or the retaining seats (12) as the uncoiled electrode portion (3) to be connected to the adapter (1) has uncoiled conductors (6).

6. The electromedical adapter (1) as claimed in claim 1, wherein the adapter (1) is configured for reversibly detachable connection to a coiled electrode portion (2).

7. The electromedical adapter (1) as claimed in claim 1, wherein the base body (7) of the adapter (1) is produced from an adapter portion (14) of a printed circuit board film (15) that is rolled up to form a hollow body, and the at least one contact element (5) is a contact surface formed on the adapter portion (14).

8. The electromedical adapter (1) as claimed in claim 1, wherein the base body (7) is at least one of cylindrical or has a round or circular cross section, at least in a plug-in region (9), the base body (7), at a free end of the plug-in region (9), has a chamfer or rounding (16) for facilitated insertion of the base body (7) into an inner longitudinal cavity (10) of the coiled electrode portion (2), or a plug element (17) corresponding to a mating plug element (18) of an uncoiled electrode portion (3) is located on the base body (7) and, in the position of use, is connected to the uncoiled electrode portion (2) via a plug connection.

9. An electromedical electrode (4), comprising at least one coiled electrode portion (2) and at least one uncoiled electrode portion (3), wherein the coiled electrode portion (2) comprises at least one coiled electrical conductor (8) and the uncoiled electrode portion (3) comprises at least one uncoiled electrical conductor (6), and the conductors (6, 8) of the two electrode portions (2, 3) are electrically connected to each other via the electromechanical adapter (1) according to claim 1.

10. The electromedical electrode (4) as claimed in claim 9, wherein the coiled electrode portion (2) is connectable, and in the position of use connected, in a reversibly detachable manner to the adapter (1).

11. The electromedical electrode (4) as claimed in claim 10, wherein the at least one coiled conductor (8) of the coiled electrode portion (2) engages externally over a plug-in region (9) of the electromechanical adapter (1) for contacting the uncoiled electrode portion (3), and the coiled electrode portion (2) for contacting the uncoiled electrode portion (3) is plugged with an attachment end (11) thereof into a socket of the electromechanical adapter (1).

12. The electromedical electrode (1) as claimed in claim 11, wherein a clear internal diameter of the coiled electrode portion (2) is smaller than a diameter of an imaginary enveloping circle which envelops the contact elements (5) located in the position of use, such that the coiled electrode portion (2) engages with radial pressure over the electromechanical adapter (1) and the contact elements (5).

13. The electromedical electrode (4) as claimed in claim 10, wherein the uncoiled electrode portion (3) is formed by a lumen tube with at least one inner lumen (20) and the at least one uncoiled conductor (6) arranged therein.

14. The electromedical electrode (4) as claimed in claim 13, wherein at least one of each said uncoiled conductor (6) of the uncoiled electrode portion (3) has a conductor end (21) which protrudes from the lumen tube (19) and which is connected in each case to a respective one of the contact elements (5) of the electromechanical adapter (1), or the at least one coiled conductor (8) of the coiled electrode portion (2) is connected in each case to a respective one of the contact elements (5).

15. The electromedical electrode (4) as claimed in claim 10, wherein each said coiled conductor (8) of the coiled electrode portion (2) contacts at least two of the contact elements (5) of the electromechanical adapter (1) in the position of use.

16. The electromedical electrode (4) as claimed in claim 10, wherein the uncoiled electrode portion (3) is produced from a flexible printed circuit board film (15) which is rolled up in the position of use to form a pipe (22) and which has, as uncoiled conductor (3), at least one conductor track (23) extending along a longitudinal extent of the printed circuit board film (15).

17. The electromedical electrode (4) as claimed in claim 16, wherein the uncoiled electrode portion (3) formed from a printed circuit board film (15) rolled up to form a pipe (22), has in an interior thereof at least one of a stabilizing support element, a support tube, a stabilizing filler, or epoxy resin.

18. The electromedical electrode (4) as claimed in claim 16, wherein the electromechanical adapter (1) is formed from an adapter portion (14) of the printed circuit board film (15) of the uncoiled electrode portion (3), the adapter portion (14) has, as the contact element (5) for each conductor track (23), a contact surface electrically connected to said conductor track (23), and the at least one contact surface (5), depending on a winding direction of the printed circuit board film (15) for producing the pipe (22), is arranged on an outer side of the pipe (22) or on an inner wall of the pipe (22) delimiting a socket of the adapter (1) for the coiled electrode portion (2).

19. The electromedical electrode (4) as claimed in claim 10, wherein the electrode (4) comprises successive ones of the coiled electrode portions (2) and of the uncoiled electrode portions (3) that are connected to each other in each case by one of the electromechanical adapters (1).

20. An electromedical pulse generator, comprising an electromedical electrode (4) as claimed in claim 10.

* * * * *